United States Patent
Gordon et al.

(10) Patent No.: US 9,201,056 B2
(45) Date of Patent: Dec. 1, 2015

(54) APPARATUS AND PROCESS FOR MEASURING PROPERTIES

(75) Inventors: Stuart Gordon, Belmont (AU); Andrzej Krajewski, Belmont (AU)

(73) Assignee: Commonwealth Scientific and Industrial Research Organisation (AU)

( * ) Notice: Subject to any disclaimer, the term of this patent is extended or adjusted under 35 U.S.C. 154(b) by 968 days.

(21) Appl. No.: 13/141,387

(22) PCT Filed: Dec. 22, 2009

(86) PCT No.: PCT/AU2009/001680
§ 371 (c)(1),
(2), (4) Date: Sep. 8, 2011

(87) PCT Pub. No.: WO2010/071929
PCT Pub. Date: Jul. 1, 2010

(65) Prior Publication Data
US 2012/0035875 A1 Feb. 9, 2012

(30) Foreign Application Priority Data
Dec. 22, 2008 (AU) .............................. 2008906569

(51) Int. Cl.
*G01N 33/36* (2006.01)
*G01N 27/22* (2006.01)
(52) U.S. Cl.
CPC ............ *G01N 33/362* (2013.01); *G01N 27/223* (2013.01)

(58) Field of Classification Search
CPC .................................................... G01N 33/362
USPC ............................................................ 702/65
See application file for complete search history.

(56) References Cited

U.S. PATENT DOCUMENTS 2,768,629 A * 10/1956 Maul ............................ 131/303
3,221,171 A   11/1965 Locher
(Continued)

FOREIGN PATENT DOCUMENTS

EP          0533079 B1   11/1997
JP          2000-46777    2/2000
(Continued)

OTHER PUBLICATIONS

Gordon et al., "Cotton: Science and technology", 2007, CRC Press, Chapter 2.*

(Continued)

*Primary Examiner* — Regis Betsch
(74) *Attorney, Agent, or Firm* — Merchant & Gould P.C.

(57) ABSTRACT

The present invention relates to an apparatus and process for measuring a property of a material such as the moisture content of cotton fiber. An embodiment is specifically adapted for determining an absolute value of the moisture content of the cotton fiber while being conveyed through ducts such as the ducts of the ginning machine. The embodiment combines large area capacitor plates with light detectors.

41 Claims, 6 Drawing Sheets (56) References Cited

U.S. PATENT DOCUMENTS

| | | | |
|---|---|---|---|
| 3,829,764 A * | 8/1974 | Bosisio | 324/632 |
| 3,996,942 A * | 12/1976 | Baier | 131/280 |
| 4,473,296 A | 9/1984 | Shofner et al. | |
| 4,649,738 A | 3/1987 | Waldie et al. | |
| 6,020,744 A | 2/2000 | Ghorashi et al. | |
| 6,476,619 B1 * | 11/2002 | Moshe et al. | 324/634 |
| 6,967,721 B2 * | 11/2005 | Moshe | 356/430 |
| 2001/0030543 A1 | 10/2001 | Joshi et al. | |
| 2003/0076118 A1 | 4/2003 | Adams et al. | |

FOREIGN PATENT DOCUMENTS

| | | | | |
|---|---|---|---|---|
| WO | WO 96/01987 | * | 1/1996 | G01N 1/20 |
| WO | 0120321 A2 | | 3/2001 | |
| WO | WO 2007/115416 A1 | | 10/2007 | |

OTHER PUBLICATIONS

Waldie et al., "Automatic Moisture Sensor for Measurement and Control of Cotton Ginning Processes", Journal of Engineering for Industry, vol. 105, Feb. 1983, pp. 27-30.*

J. Hearle, Chapter 2: "Physical structure and properties of cotton", 2007, Gordon et al., "Cotton: Science and Technology" CRC Press.*

A.H. Waldie, S.E. Hughs and M.N. Gillum, "Automatic Moisture Sensor for Measurement and Control of Cotton Ginning Processes", Journal of Engineering for Industry, vol. 105, Feb. 1983, pp. 27-30; ASME.

Authorized officer Stephen Bewlay, International Search Report in PCT/AU2009/001680, mailed Apr. 16, 2010, 3 pages.

Supplementary European Search Report for corresponding European Patent Application No. 09833929 mailed Jul. 7, 2014.

* cited by examiner

APPARATUS AND PROCESS FOR MEASURING PROPERTIES

FIELD OF THE PRESENT INVENTION

The present invention relates to an apparatus for measuring properties of fibrous and non-fibrous materials. For example, and without limitation, the present invention may be suitable for measuring moisture levels of fibrous materials such as cotton while being handled by processing machinery.

BACKGROUND OF THE PRESENT INVENTION

With respect to cotton, the level of moisture at harvest through the lint in the bale can have significant effects on the quality of fibre sold to the spinning mill. There are optimum moisture levels for seed-cotton and lint that provide good and efficient ginning, cleaning, baling and safe storage. Likewise there are similar considerations in the processing of other materials and fibres. In the case of moisture, to optimise processing and fibre quality the amount of moisture in a fibre under ambient conditions needs to be balanced with the amount of drying or moisture applied during the various processes.

Despite development of apparatuses that measure and then allow drying or moisture replenishment to be metered onto fibre there has not been widespread uptake due to disadvantages associated with the measurement technique. The main disadvantages of current moisture measurement techniques are their low accuracy and/or that a long time period is required to conduct the tests.

The techniques currently used for measuring the moisture in cotton lint can be classified into five groups. The techniques that are currently used are typically based on either one of:
thermal drying (gravimetric);
chemical reaction analysis;
spectroscopy;
electrical resistance or microwave transmission of water; and
compression and resiliency properties of fibre.

The use of thermal, chemical and compression methods is excluded from in-line applications on the basis of inadequacy of measurement speed.

Electrical resistance and microwave transmission can be used for in-line applications or in situ. However, both techniques have shortcomings. For instance, resistance meters is carried out using electrode probes that are affected by surface contaminants, which can alter immediate and short-term future readings, and measurements are diminished by very wet or very dry samples, which affect the accuracy of resistance readings. Moreover, resistance apparatuses measure only a small part of the production; hence the problem with contamination of electrodes.

Microwave radiation transmission relies on the sample having a minimum density between the microwave transmitter and antennae. For example, microwave apparatuses are applied very successfully at either end of the cotton ginning process, i.e. to modules of seed-cotton and to compressed bales of cotton lint, where the density of the accumulated fibre is in excess of 100 $kg/m^3$. The application of microwave apparatuses to transport ducts where the density of material is less 15 $kg/m^3$ is considered not viable.

It is an object of the present invention to provide an alternative apparatus and process that can be used to measure, amongst other things, the moisture levels of materials such as fibrous materials.

SUMMARY OF THE PRESENT INVENTION

Apparatus

The present invention relates to an apparatus for measuring a desired property of a material, the apparatus including:
  i) an electric field generator and when in use, the material whose desired property is to be measured is disposed in the electric field and changes in the electric field caused by the material provides a first output that is related to at least two properties of the material, at least one of which is the desired property and a second property;
  ii) a device that provides a second output that is related to the second property of the material; and
  iii) a processing unit that determines the desired physical property of the material with reference to the first and second outputs.

Throughout this specification the term "processing unit" is used to refer generically to any device that can process instructions and may include: a microprocessor, microcontroller, digital signal processor, programmable logic device, field programmable gate array (FPGA), application specific integrated circuit (ASIC) or other computational device, a general purpose computer (e.g. a PC) or a server.

Changes in an electric field caused by the presence of a material can be used to determine properties of the material. The electric field generator can be any electronic device which generates an electric field into which the material may be introduced. For example, the electric field may be a generated using inductor coils or capacitor plates. An advantage of using inductor coils or capacitor plates is the electric field generator can also operate as a sensor to detect changes in the electric field caused by the presence of the material in the electric field. However, separate electric field generator and sensors may be used.

In an embodiment the electric field generator is implemented in the form of a capacitor comprising at least one pair of capacitor plates arranged opposite and parallel to each other with a space in between whereby air and the material between the plates provides a dielectric.

In an embodiment, the physical property is the moisture content of the material and the second property is the mass of material, and suitably the mass of the material in the electric field.

Throughout this specification the terms "moisture of the material", "moisture content of the material" or variations thereof is defined as the ratio of mass of absorbed water of the material to the total material mass. For example in the situation when the material is cotton fibre, the moisture content of the cotton is a ratio of the mass of absorbed water of the cotton to the lint or seed-cotton mass. The mass of water absorbed by the material may be determined using any suitable method, for example, using standard thermal gravimetric methods.

In an embodiment the apparatus includes a passageway, suitably in the form of a duct through which the material being measured is conveyed. For example, the material is pneumatically conveyed along the duct.

In an embodiment, the electric field extends across the passageway and the first output is based on the changes in the electric field as the material is conveyed along the duct and through the electric field. In addition, the device measures the second property of the material as the material passes through the electric field.

Although it is possible that the device may be balance scales or even a second electric field generator, suitably, the device is an optical device that estimates the mass of the material in the electric field.

Suitably, the optical device comprises a light source and a light receiver that are arranged such that the material at least in part, is located between the light source and the light receiver and the second output is an output signal of the light receiver. Changes in the amount of light received by the receiver caused by the material shielding the receiver is a function of the mass of the material.

In an embodiment, the optical device is configured to radiate the material in the electric field with light that may extend into the UV and/or NIR spectrums. Suitably, the optical device radiates the material as it passes through the electric field.

In the situation in which the apparatus is operated to measure the moisture content of a fibre such as cotton fibre, suitably the electric field generator is operated to generate an electric field that is sensitive to the presence of the material. For this embodiment, we have found that we can adjust the electric field such that it is suitable for measuring a sample of cotton fibre having a total mass up to approximately 4,000 grams in the electric field, and suitably up to 2,000 grams and even more suitably in the range of 200 to 900 grams. These operating parameters are suitable for measuring moisture content of natural fibre up to 20% and, when the fibre is cotton, changes in electric field of this strength is suitable for measuring a moisture content in the range of 0.1% to 16% weight of the fibre.

In an embodiment, the electric field generator includes a capacitor. The capacitor comprises charged plates, suitably copper plates that have dimensions encompassing the width of the passageway or the conveyance duct.

In an embodiment, the apparatus further includes a converter that converts either one or a combination of the first and second signals from an analogue signal to a digital signal.

Some embodiments include output converters adapted to transform the first output and second output into first and second output signals of the same type. For example, where the first output and second output are not of the same type and therefore unable to be directly compared, output converters can be used to transform the outputs into output signals of the same type.

In an embodiment where a capacitor is used to generate the electric field and the first output is a difference in capacitance, a first converter can be used to convert capacitance difference to a voltage difference signal. If in this embodiment the second output is indicative of a light signal, then a second converter can be provided to convert the second output from the light detector to a voltage signal. Conditioners may also be provided to enable the magnitude of the first and second signals to be adjusted, if necessary, to enable direct signal comparison. It should be appreciated that the converters and any conditioners may be implemented using electronic circuits and the circuit configuration for each converter and conditioner will vary depending on the embodiment.

It should be appreciated that instructions for determining the desired property of the material with reference to either of: i) the first and second outputs, or ii) the first and second outputs after being converted or conditioned by the converters of conditioners, may be implemented using a software program executable by the processing unit. Alternatively the instructions may be implemented in hardware, for example hardcoded into an ASIC or hardwired into a logic circuit. Alternative embodiments may use a combination of hardware, firmware and software for implementing a processing unit adapted to determine the desired property of the material with reference to the first and second outputs, or the voltage difference signal and voltage signal either with or without conditioning.

In an embodiment, the processing unit calculates the moisture content of the material with reference to either: i) the first and second outputs; ii) the first and second output signals; or iii) the voltage difference signal of the first converter and voltage signal of the second converter.

In an embodiment, the apparatus further includes a temperature sensor for sensing the temperature in the electric field. The temperature sensor may be any suitable thermocouple device. A signal from the temperature sensor may be communicated to the processing unit and the processing unit may activate an alarm when the operating temperature falls outside upper and lower preselected temperature limits.

In an embodiment, the apparatus further includes a humidity sensor for sensing the humidity of air in the electric field. A signal from the humidity sensor may be communicated to the processing unit and the processing unit may activate an alarm when the operating humidity falls outside an upper preselected humidity limit.

In an embodiment, the processing unit estimates the relative humidity in the electric field from outputs of the temperature and humidity sensors.

In an embodiment, the processing unit calculates the moisture content as a function that includes variables based on:
the first output representing changes in the electric field, and suitably the voltage difference signal of the first converter;
the second output that is the form of an output of the optical device, and suitably, and voltage signal of the second converter; and
an estimate of the relative humidity of in the electric field.

In an embodiment, the apparatus further includes a flow sensor for sensing the flow rate of air in the electric field. Under most operating conditions, the flow rate of air can be equated to the flow rate of material passing through the electric field.

In an embodiment, the apparatus further includes a shield about the electric field to prevent interference from other electromagnetic fields from external sources.

The present invention also relates to an apparatus suitable for measuring a physical property of a material, the apparatus including:
i) an electric field generator and when in use, the material whose physical properties is to be measured is disposed in the electric field and changes in the electric field caused by the material provides a first output;
ii) a device that provides a second output that relates to properties of the material; and
iii) a processing unit that determines for the desired property of the material with reference to the first and second outputs.

In an embodiment, the first output signal relates to at least two properties of the material in the electric field, at least one of which is the desired property and a second property.

In an embodiment, the second output signal relates to the second property of the material.

Process/Method

The present invention also relates to a process for determining a desired property of material, the process including the steps of:
a) introducing material into an electric field;
b) measuring changes in the electric field caused by the material introduced into the electric field in step a), wherein the change in electric field relates to the desired property of the material and another property of the material in the electric field;
c) estimating the other property of the material;

d) determining a value for the desired property using the changes in electric field measured in step b), and the other property of the material from step c).

Embodiments can also include an initial step of generating an electric field.

In an embodiment, step a) involves conveying the material through the electric field. Suitably, step a) involves conveying the material pneumatically through the electric field. Suitably, a stream of air carrying the material travel at up to 30 m/s and even more suitably up to 20 m/s.

In an embodiment, the change in electric field according to step b) relates to at least two properties of the material in the electric field, of which one is the desired property and another is the mass of the material in the electric field (i.e., the mass of the material itself and moisture of the material).

In an embodiment, the desired property of the material is moisture content of the material.

The electric field may be generated by any suitably electric field generator.

Changes in the electric field may be measured by any suitable sensor. In an embodiment, the changes in the electric field are sensed as an output of the electric field generator.

In an embodiment, the electric field is capacitively generated, i.e. by a capacitor, or inductively generated by an inductor.

In an embodiment, estimating the property of the material according to step c) is based on an output of an optical device in which the output is representative of mass of the material sensed by the optical device.

In an embodiment, the optical device includes a light source and a light receiver, and the output of the optical device is based on amount of light received by the light receiver. In other words, estimating the mass of the material involves exposing the material to a light source and light transmitted or reflected by the material and received by the light receiver is function of the mass of the material (which we can assume to approximate the dry mass of the material). Even more suitably, the light source and light receiver are arranged such that at least part of the material is located between, or passes between, the light source and the light receiver. We have found the changes in an amount of the light received by the light receiver from the light source relates to the mass of the fibre located between the light source and the light receiver.

In an embodiment, the method includes transforming the output of the electric field generator and the output of the optical device into first and second output signals of the same type. For example, where the first output and second output are not of the same type and therefore unable to be directly compared, output converters can be used to transform the outputs into output signals of the same type.

In an embodiment where changes in the electric field are measured by changes in capacitance of a capacitor that generates the electric field, the output of the capacitor may be transformed from an a capacitance difference into a voltage difference signal. In other words, in the situation in which a capacitor is used to generate the electric field and measuring changes in the electric field is a function of the capacitance of the capacitor, a first converter may be used to transform the capacitance difference into a voltage difference signal.

In an embodiment where the other property of the material is based on the output of the optical device that represents the mass of the material in the electric field, the output of the optical device may be transformed into a voltage signal.

In an embodiment, the magnitude of either one or both of the voltage difference signal and the voltage signal is adjusted to enable the magnitude of the voltage difference signal and the voltage signal to enable direct signal comparison.

In an embodiment, step d) includes calculating a desired property of the material as a function of the voltage difference signal of the capacitor and the voltage signal of the optical device.

In an embodiment, the process also includes measuring the temperature of the air in the electric field of the capacitor using a temperature sensor, or suitably the air flowing through the electric field of the capacitor.

In an embodiment, the process also includes estimating the relative humidity of the air in the electric field of the capacitor using a humidity sensor and the output of the temperature sensor, or suitably the air flow through the electric field.

In an embodiment, step d) includes calculating the moisture content of the material in the electric field as function of: i) the voltage difference signal of the capacitor; ii) the voltage signal of the optical device; iii) the relative humidity estimation.

In an embodiment, step d) includes calculating the moisture content of the material using the formula:

$$\text{Moisture} = f(M_{cap}, M_{light}, H, T) + k$$

wherein $M_{cap}$ is the mass indicated by the output of the capacitor such as the voltage difference signal (mentioned above), $M_{light}$ is the mass indicated by the output of the light sensor such as the voltage signal (mentioned above), H is the humidity, T is the temperature, and k is a constant representative of a number of parameters that will depend on the specific apparatus geometry and sensors.

It is understood that empirically established constants ($k$-$k_1$, $k_2$, $k_3$, $k_n$) will arise during the calibration process and may change with factors such as the dimensions of the capacitive sensor/capacitor, different types of light sensors, and humidity and temperature sensors.

In an embodiment, the determinations or calculations of step e) are preformed using a processing unit.

Although the process may be suitable for handling a range of different types of materials, in the situation in which the material is a fibre such as cotton fibre, the desired physical property is moisture content of the fibre. The electric field is sensitive to a total mass of the fibre in the electric field of up to approximately 4,000 grams, and suitably up to 2,000 grams and even more suitably in the range of 300 to 800 grams.

In the situation in which material is cotton fibre and measuring the moisture content of the fibre is the objective, step e) suitably involves determining the moisture content to an accuracy of ±0.5% weight of water on the weight of the fibre, or even more suitably to an accuracy of ±0.25%.

In an embodiment, the process may involve controlling the flow rate of material passing through the electric field.

In an embodiment, the process may involve controlling the humidity of the air passing through the electric field.

In an embodiment, the process may include controlling the electric field.

In an embodiment, the process may involve measuring any one or combination of the following operating conditions and activating an alarm when the operating condition falls outside a predetermined limitation for the operating condition.

According to the present invention there is provided a process for determining moisture content of cotton fibre, the process including the steps of:

a) conveying a stream of cotton fibre through an electric field of a capacitor;

b) measuring changes in the capacitance of the capacitor as a result of the fibre passing through the electric field;

c) estimating the mass of the fibre in the electric field based on an optical measurement of the fibre in the electric field; and d) determining the moisture content of the fibre based on the changes in capacitance measured in step b) and the mass of the material of step c).

Estimating the mass of fibre in the electric field based on the optical measurement may be performed by comparing values of the optical measurement with a known set of reference data such as reference data for weighed samples of cotton fibre.

According to the present invention there is also provided a process for determining a physical property of a material, the process including the steps of:

a) introducing material into an electric field of a capacitor;

b) measuring changes in the capacitance of the capacitor caused by the material introduced into the electric field in step a) for a given mass of material in the electric field; and c) determining an absolute value for the physical property based on changes in capacitance measured in step b) with respect to a known set of reference data for the type of material in the electric field.

It will be appreciated that the process of the present invention, either in its broadest form or an embodiment thereof may also include any one or a combination of the features described above under the heading Apparatus. Similarly, the apparatus of the present invention, either in its broadest form or an embodiment thereof may also include any one or a combination of the features described above under the heading Process/Method.

BRIEF DESCRIPTION OF THE DRAWINGS

The present invention will now be described with reference to the accompanying drawings, of which.

DETAILED DESCRIPTION

An apparatus and process of a preferred embodiment of the present invention will now be described with reference to the accompanying Figures. The apparatus and process shown in the Figures is also specifically adapted for measuring the moisture content of cotton fibres such as loose cotton fibre flowing pneumatically or by other means including gravity. However, it will be appreciated that the invention may be used with respect to other types of the materials or fibres and may also be used for measuring different types of properties of the material being measured. For instance, the apparatus and method may also be applicable to seed-cotton, ginned seed and other grains.

Figure 1:
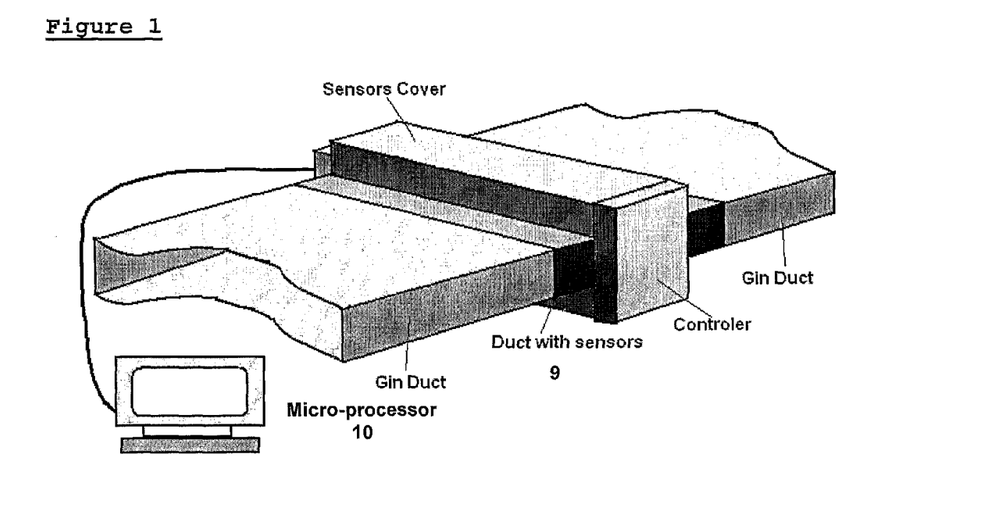
FIG. 1 is a schematic perspective view of a apparatus for measuring moisture of cotton fibre flowing in a duct of the cotton gin according to a preferred embodiment.
Figure 2:
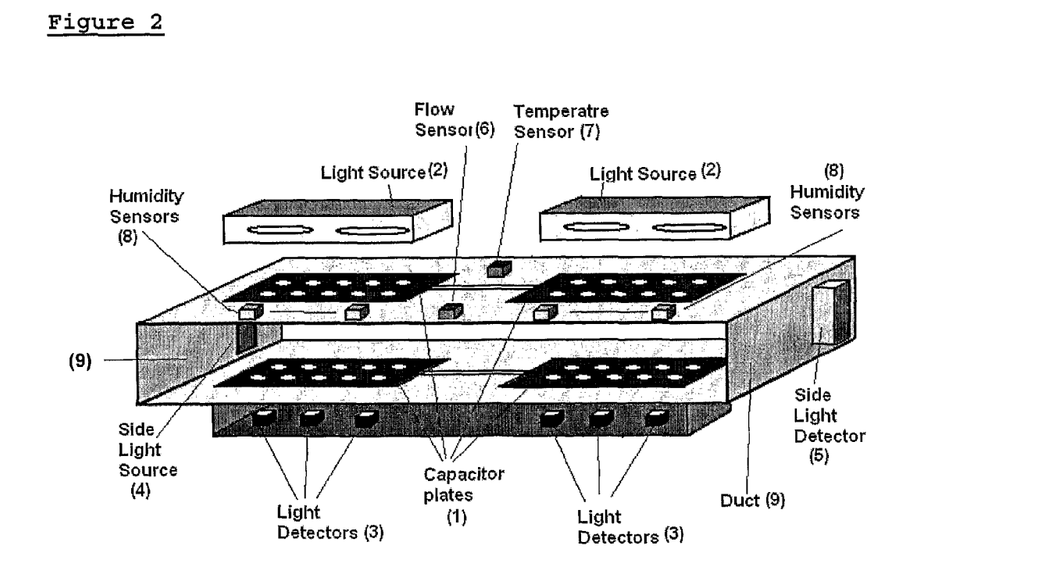
FIG. 2 is a schematic exploded view of the working components of the apparatus shown in FIG. 1 including capacitor plates and an optical device for measuring the moisture content of cotton fibre.

With reference to FIGS. 1 and 2, the apparatus includes a duct or conduit that can be retrofitted to existing ginning equipment to allow an in-line or in-situ testing of the fibre. The size of the duct can be modified as required to suit particular types of ginning equipment. In particular the duct 9 shown in the Figures is designed to fit to a ducting between a gin stand and a lint cleaner of cotton processing equipment and is adapted so that a stream of fibre entrained in air flows along the duct 9. The duct of the lint cleaner is a rectangular duct in the order of 150 mm by 2400 mm.

The apparatus includes a capacitor suitably in the from of two pairs of copper capacitor plates 1 on upper and lower sides of the duct 9 that are mounted on fibre glass, and an optical device in the form of an array of LEDS 2 and 4 that are located in top and left sides of the duct respectively and light receivers or photo-optic sensors 3 and 5 located on the bottom and right hand side of the duct 9 respectively that are coupled to a digital micro-processing unit 10 and personal computer.

Air or any other material in the space between the plates acts as a dielectric between the capacitor plates 1. Thus, introducing a material into the space between the capacitor plates can causes a change in the electric field by changing this dielectric which in turn is observable as a change in capacitance of the capacitor.

In use, cotton fibre is conveyed through the electric field of the plates 1 of the capacitor. The capacitor is supplied pulsed excitation. Changes in capacitance of the capacitor are converted from an analogue to digital signal by the convert and supplied to the microprocessor.

Changes in capacitance are a function of the mass of the fibre and the moisture content of the fibre. Ideally, changes in the electric field caused by the fibre passing through the electric field are resolved in terms of the changes in capacitance. In practice we have found that the electric field can provide a resolution in the order of 0.015 grams i.e., 0.1% or 0.2 grams of a 200 gram sample of the cotton fibre in the electric field. We have also found that up to 4,000 grams of fibre can be entrained in air passing between the plates. These operating parameters have proven suitable for measuring moisture content of the fibre of approximately 0.1 weight % at very low relative humidities near 0% to approximately 16 weight % at almost 100% relative humidity.

The array of LEDS 2 at the top, and optionally at the bottom of the capacitor plates 1 are connected to a pulsed current source, which allows greater light output over time and reduces the influence of ambient light on the sensors. The additional set of LEDS 4 placed at the side of the duct are also connected to a pulsed current source but suitably at a different frequency to the frequency to that of LEDS 2. A different switching light frequency allows differentiation between the two light sources using simple Fast Fourier Transform analysis (FFT).

In the event of high fibre weight between the LEDS and the light receivers, the light power can be increased by increasing the amplitude of current pulses and accommodating the logarithmic amplifiers for the light receivers. If heavier weights of material are used, and the transmitted light power is occluded by the fibre, the mass flow may be predicted by the scattered light from the top surface of the moving fibre.

The light radiating from the LEDS 2 or 4 that is not shielded or by the fibre passing through the duct 9 is detected by the light receivers 3 and 5. We have found that the light received by the receivers 3 and 5 and, therefore, the output of the light receivers is related to mass of the fibre passing through the duct 9 at any moment. Moreover, the particular arrangement of the LEDS 2 and 4 and light receivers 3 and 5 on outsides of the capacitor plates 1 as shown in FIG. 2, ensures that the mass of the fibre detected by the optical device is the mass of fibre in the electric field of the capacitor.

The perforated capacitor plates 1 are placed on the both sides of the duct 9 on glass or fibreglass sheets in order to prevent them touching the duct 9 or conduit chassis. A cover is fitted over the capacitor plates 1 to minimise the impact of the external electromagnetic fields over the fibre passing between the capacitor plates 1.

The two sets of capacitor plates measure the permittivity ($\in$) of the ducting material (fibreglass) and the air and material i.e., the cotton and moisture moving between the plates.

$$\in_{total} = \in_{cotton+moisture} \in_{airhumidity} \in_{fibreglass} \qquad \text{Eq 1}$$

Significant changes in permittivity between the capacitor plates are related to changes in the permittivity of the cotton and the moisture content of the cotton. Variations in permittivity associated with changes in air humidity in the ducting contribute to a level of stray-capacitance. However, we have successfully implemented the device on the basis that stray-capacitance is correctable by taking into account the temperature and humidity levels measured in the duct. The total capacitance of the device may therefore be represented by the equation:

$$C_{total} = C_{stray} + \left(\frac{\varepsilon_{total} * A * (n-1)}{d}\right) * f \qquad \text{Eq 2}$$

where A=the copper plate surface constant in m2, n=number of plates, d=distance between the plates in m and f=capacitor edge field coefficient. The permittivity of the fibreglass (or glass) used to support the capacitor plates is constant and is taken into consideration during design. Due to the distance between the capacitor plates of around 150 mm being constant, the edge field is also constant.

The range of moisture values observed in the cotton moving through the device is encapsulated in a capacitance range of between 10-17 pF. The mass of cotton and the mass of moisture are highly correlated so there is a need to normalise the mass component of the capacitance signal to achieve the moisture content of the cotton. The LED light sources and photo-optic sensors 5 and 6 of the optical device are used to estimate the mass of fibre between the capacitor plates at any one time. Light passing through the cotton, or for that matter any particulate material being measured by the apparatus can be can described by the Lambert-Beer Law.

$$I = I_o * f(x \cdot c) \qquad \text{Eq 3}$$

where I=the incident light from the source flux, $I_o$=source light flux, x=distance between light source and sensor (mm), k=excitation co-efficient and c=concentration of material in the specified volume. This law is applicable here because the output signal of the photo-sensor 5 and 6 is averaged over several seconds, and can be envisaged as a response to the particles (the cotton or seed-cotton) suspended in a fluid. The distance between the light source and sensors 5 and 6 is fixed (at around 350 mm). The amount of light transmitted through to the sensors depends on the concentration or mass of fibre in the duct. Cotton fibre is highly reflective of light, so the sensors 3 and 5 are capable of measuring both occluded and scattered light.

The array of LEDS 2 is placed directly above the top (or below the bottom) of the capacitor plate 1 so the light can travel through the mesh or holes in the capacitor plates 1. Partially transparent glass finished with vaporised metal can be used instead of the perforated capacitor plates 1. The photo-optical sensors 3 are placed directly below the bottom or above the top of the capacitor plate 1 so that light directed through the perforated plates can reach the photo-optic sensors 3. An example of suitable LEDs includes LED lamps having the power of 24V & 1.3 A and can be obtained from TENROD Australia. An example of suitable photo-optical sensors includes photodiodes manufactured by OSRAM GmbH under the trade name SFH213 PIN photodiodes.

The capacitor plates 1 may be substituted with multiple plates that are connected in series or parallel. Moreover, it is possible that the optical device for detecting the mass of fibre in the electric field of the capacitor be substituted with another capacitor operating under conditions suitable for measuring the mass of the fibre conveyed through the duct.

The temperature sensor 7 of the apparatus is an on-the-shelf temperature transducer and humidity sensor 8 that gives output voltage signals related to temperature and humidity. Any suitable sensor can be used, and by way of example, we used a temperature sensor supplied by Innovative-Sensor Technology under the brand TSic 301 temperature transducer and a humidity sensor supplied by Honeywell under the brand HIH 4000 Integrated Circuitry humidity transducer.

To provide accurate results for the relatively small capacitance changes, it is preferable to convert the capacitance changes output into an output signal over a broader voltage range using a capacitance-to-voltage converter.

Figure 4:
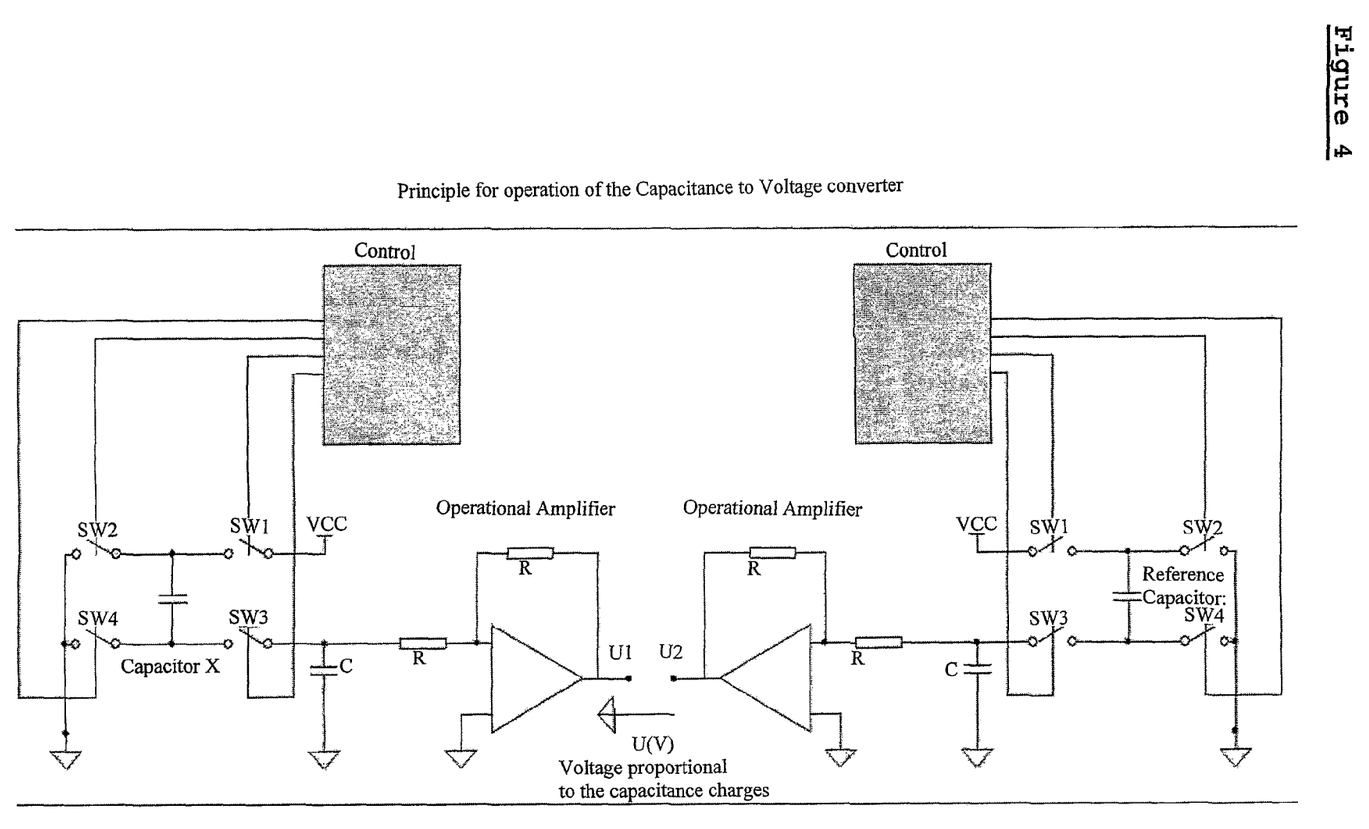
FIG. 4 is a circuit diagram of a first converter for converting a output of the capacitor shown FIGS. 2 and 3 into a voltage difference signal relating to the mass of the material in the capacitor.

An example of a capacitance-to-voltage converter comprising a reference stage and a measuring stage is illustrated in FIG. 4. The reference stage includes a reference capacitor having a known capacitance connected to an operational amplifier. The reference capacitor can be a fixed capacitance capacitor. The measuring stage includes the capacitor formed across the gin duct connected to an operational amplifier. The capacitance of this gin duct capacitor varies in accordance with the cotton introduced into the dielectric. Each of these stages is controlled by a control module for connecting and disconnecting the circuits to the power supply. The control module controls the power supply to provide pulsed excitation of the circuits. The difference between the voltage of the operational amplifier output of the reference stage and the operational amplifier of the measuring stage is proportional to the capacitance change of the gin duct capacitor.

Figure 5:
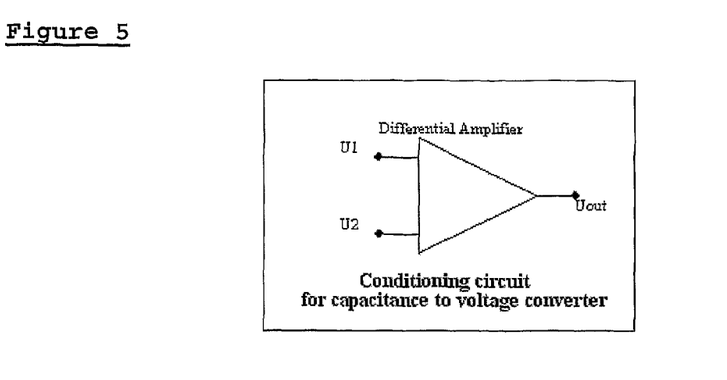
FIG. 5 is a conditioning circuit for adjusting the magnitude of the voltage difference signal provided by the circuit of FIG. 4.

A conditioning circuit, for example, in the form of a differential amplifier as illustrated in FIG. 5, can be provided to combine the output of the reference stage and measuring stage into a signal output signal. Although this example is illustrated using an operational amplifier circuit and differential amplifier, alternative circuit configurations are envisaged. A person skilled in the art will also appreciate that different converter circuits will need to be used where alternative electric field generation and sensing circuits are used. Further alternative circuits using direct or alternating current sources rather than pulsed current sources, may also be used.

Data received from the converter illustrated in the FIG. 4 is acquired via an analogue-to-digital converter and then fed into a micro-processor and a PC.

The light-to-voltage converter is constructed so that the output of the photo-sensors, which is based on the light received by the photo-sensors, is related to the mass of the cotton.

Figure 6:
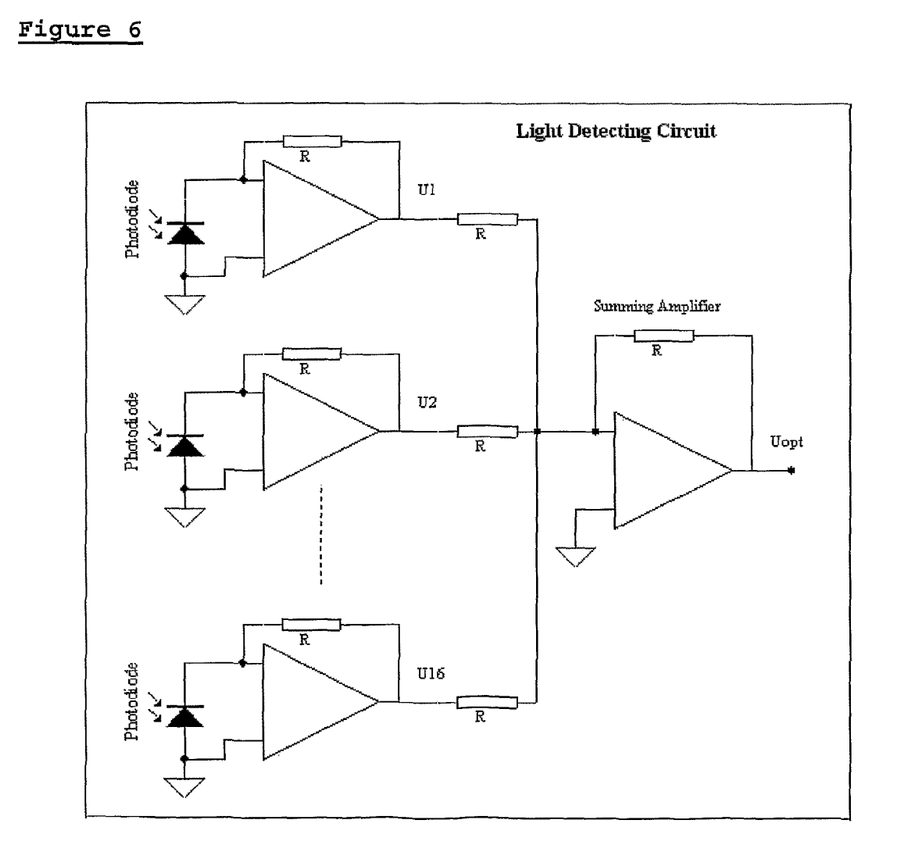
FIG. 6 is a circuit diagram for converting the output of light detectors/receivers of the optical device shown in FIGS. 2 and 3 device into a voltage signal relating to optical measurement of the mass in the electric field.

For example, the light-to-voltage converter can be adapted to transform the output from individual photo sensors into a single voltage signal indicative of the mass of cotton passing through the test rig. In an embodiment the light-to-voltage converter aggregates the output from each of the photo-sensors. For example, as illustrated in FIG. 6, each photo-sensor of a set of photo-sensors can be a photodiode. This example uses photo-diodes as photo-sensors, however, a person skilled in the art will appreciate that any photo-sensor may be used and all alternatives are contemplated within the scope of the present application and accompanying claims. The output of each photodiode can be amplified using an operational amplifier and summed using a summing amplifier to provide an aggregated voltage signal for the set of photo-sensors.

Figure 7:
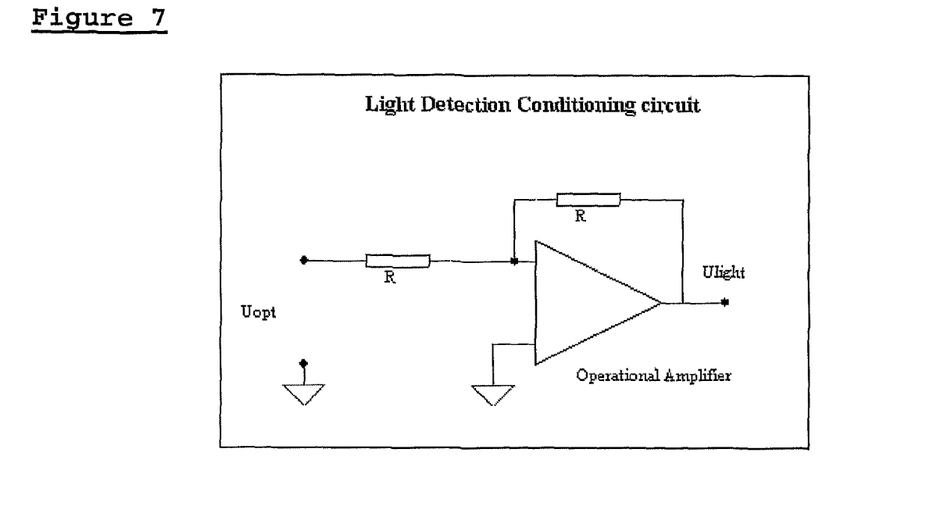
FIG. 7 is a conditioning circuit for adjusting the magnitude of the voltage signal produced by the circuit of FIG. 6.

Optionally the light-to-voltage converter can also be provided with a conditioner stage whereby the magnitude of the output voltage signal can be adjusted if necessary. For example, a light detection conditioning circuit can be implemented using an operational amplifier as illustrated in FIG. 7. The light output conditioner circuit may be omitted in some embodiments. Alternatively, in some embodiments the light detection conditioner can be incorporated in the light-to-voltage converter.

In the illustrated embodiment the light-to-voltage converter and light detection conditioning circuits are implemented using operational amplifiers, it should be appreciated that this is only one example of how such circuits may be implemented. Alternative circuit configurations will be apparent to a person skilled in the art, for example circuits using transistors and passive components or complex integrated circuits are also envisaged. All suitable alternative circuits are envisaged within the scope of the present application and accompanying claims.

The capacitor plates, LED light courses and light receivers were then incorporated into an industrial scale apparatus as shown in FIG. 2 for retrofitting to a duct interconnecting the gin stand and first lint cleaner.

Figure 3:
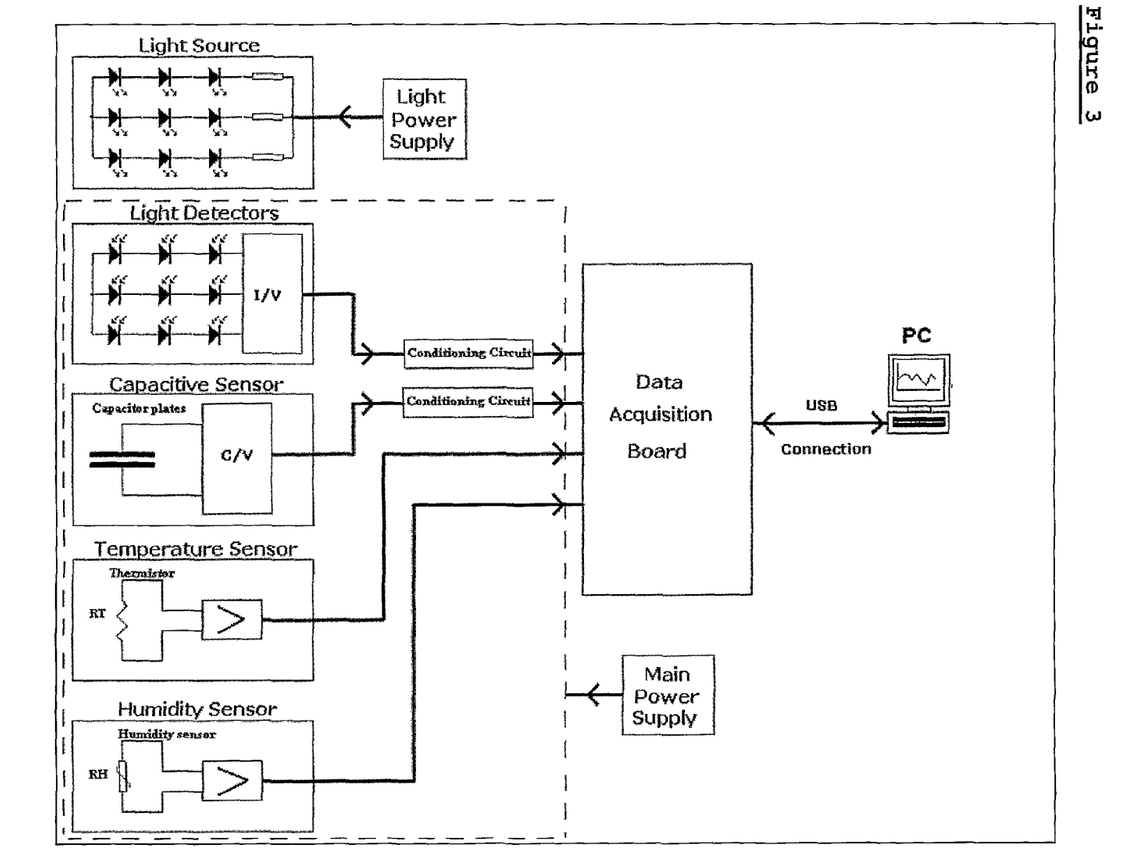
FIG. 3 is block diagram of the electrical components associated with the apparatus shown in FIGS. 1 and 2.

FIG. 3 is a block diagram of the main electrical components of the apparatus. Specific details of suitable light sources, light photo-sensors, capacitor plates, temperature sensors, humidity sensors, capacitance-to-voltage converter, and light-to-voltage converter have been described above.

The capacitance-to-voltage and light-to-voltage converters together with off-the-shelf temperature and humidity transducers were coupled with a National Instrument NI-USB-6216 data acquisition unit and connected to an ARK-3399 computer that was used to process and save data received. The capacitance sensors delivered linear and rapid responses to variations in cotton mass and moisture to a sensitivity of ~±1 femtofarad of the nominal capacitance value. The effect of external electrical field disruptions was reduced by shielding the electronic circuitry and cables. Sensors and light sources were sealed from the outside environment so that dust would not affect the measurement. The position of the glass window used to separate the light sensors from the material and dust inside the duct means that it was largely self-cleaning.

Design features of this device included the previously mentioned approaches for reducing stray-capacitance, incorporating humidity and temperature sensors and the alignment of high precision capacitance-to-voltage and light-to-voltage converters. The output of the capacitance-to-voltage converter in the industrial device covered a range between 1V to 12V that enabled high resolution capacitance changes between 10 pF and 17 pF to be recorded.

The data acquisition unit was set to average each the output signals and store the data every 60 seconds. This allowed a reasonable sample frequency and in view of the withdrawal of fibre sampling for off-line moisture measurement in order to calibrate the apparatus.

Finally, the apparatus was fitted between a gin stand and a first lint cleaner, and calibrated to ensure that the output signals of the capacitor, light detectors, temperature and humidity sensors were accurately correlated to the moisture content of the fibre.

The calibration technique included fibre conveying between the capacitor plates of the apparatus being sampled over two separate one-week periods and the moisture content of the fibre sampled being accurately measured off-line. The time at which the samples were taken was synchronized with an on-line clock of the PC to allow the data outputs to be matched with the off-line measurements.

Off-line measurements of the moisture content of the cotton fibre can be measured quickly using a VOMAX 465 Bench Top Moisture Gauge manufactured by VOMAX Instrumentation Inc., Adelaide, South Australia. The VOMAX 465 Instrument was calibrated to a gravimetric moisture content according to an oven-drying standard similar to ASTM Standard designated 2495-07. A reported correlation between moisture content by oven-drying and the VOMAX 465 for cotton fibre samples with moisture contents between 4 and 10% was 0.964, with a standard error of (moisture) prediction of ±0.36%.

By an iterative process we have devised a formula for the moisture content of the fibre measured by the apparatus having the form:

$$\text{Moisture} = f(M_{cap}, M_{light}, H, T) + k \qquad \text{Eq 6}$$

wherein
$M_{cap}$ is the mass indicated by the output of the capacitor such as the voltage difference signal (mentioned above),
$M_{light}$ is the mass indicated by the output of the light sensor such as the voltage signal (mentioned above),
H is the humidity,
T is the temperature, and
k is a constant representative of a number of parameters that will depend on the specific apparatus geometry and sensors.

In its simplest form the moisture content of the fibres is function of variables based on the outputs of the capacitive and light sensors, the humidity sensor and the temperature sensor (or the relative humidity).

By way of example only, we have found the formula of the same general form of Eq 6 may be expressed as set out below in Eq 7. However, it should be appreciated that Eq 7 is only suitable for the specific geometry of the apparatus tested and other parameters such as the sensor types. The moisture values for the fibre was determined from the capacitor and light sensor outputs when corrected for atmospheric humidity and then aligned and rescaled with average moisture content values from the VOMAX 465, to provide:

$$\text{moisture} = \left( A \frac{M_{cap}}{B * M_{light}} + d \right) * m_{VA} - C * H_{true}(T) \qquad \text{Eq 7}$$

where $M_{cap}$ is the mass indicated by the capacitance sensor, $M_{light}$ is the mass indicated by the light sensor, $m_{VA}$ (in %) is a rescaling factor determined by the average moisture content (over the calibration test period) measured by the VOMAX 465 and $H_{true}$ is the relative humidity. The value of $m_{VA}$ used in these tests was 5.5%. Four other constants are used: A and d allow for the rescaling and alignment of the normalized capacitance signal to the final moisture value, while B depends on the difference between the cotton mass as indicated by the capacitor and light sensors. During the testing reported here, the value of B was determined as being ~1.12, but it is possible for the value of B to be affected by changes in the dimensions and orientation of the capacitor and/or light sensors. The constant C describes a portion of the in-duct humidity that is subtracted from the capacitance signal to compensate for external humidity and temperature changes that affect the permittivity of the sensor materials in the capacitor. This constant is positive and ranges in magnitude from 0.1 to 0.001. In the trials, C has a value of 0.0012. Values of A and d were 0.8 and 0.7 respectively. Constants A, B, and C are empirically established during the calibration process and they may change for different dimensions of the capacitive sensor, different type of light sensor, and humidity and temperature sensors.

The apparatus is designed to be fast so that each individual scan of the fibre takes very little time and the material moves only by the distance of the physical width of the capacitor per scan. The signals can be processed in real time before the next scan. The resolution of the apparatus therefore depends on the speed of the cotton in the duct. At 20 m/sec this associates with a time between scans of less than 10 milli-seconds, which allows the material to travel 0.2 m matching the width of the capacitor sensor. The scanning process is continuous and reliability of the apparatus is enhanced by detecting the mass in the electric field and measuring changes in capacitance substantially simultaneously.

Figure 8:
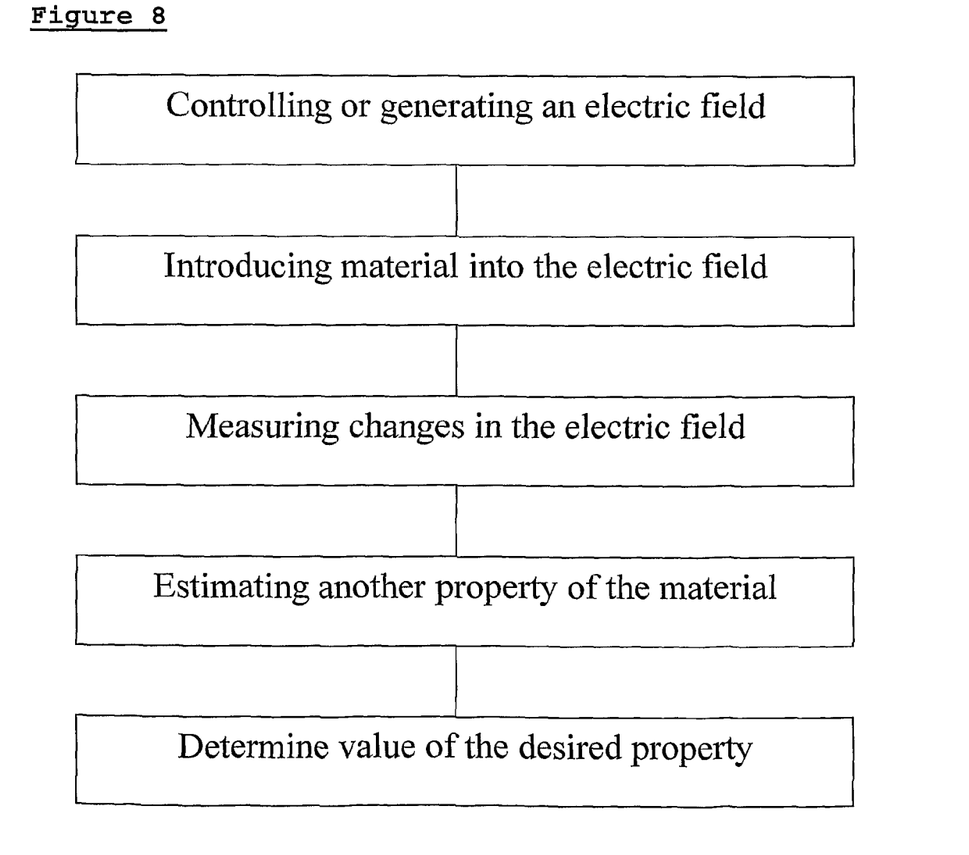
FIG. 8 is a block diagram showing some of the main steps of the process according to an embodiment of the present invention.

With reference to FIG. 8, the process of the preferred embodiment may be summarised as by the steps of:
i) introducing material into the electric field, suitably by conveying cotton fibre through the electric field;
ii) measuring changes in the electric field caused by the material introduced into the electric field, which is representative of at least 2 properties of the material including a desired property that is being determined and another property;
iii) estimating the other property of the material;
iv) determining a value for the desired property; and optionally
v) controlling or generating the electric field.

It will be understood by persons skilled in the art of the invention that many modifications may be made without departing from the spirit and scope of the invention.

Figure 9:
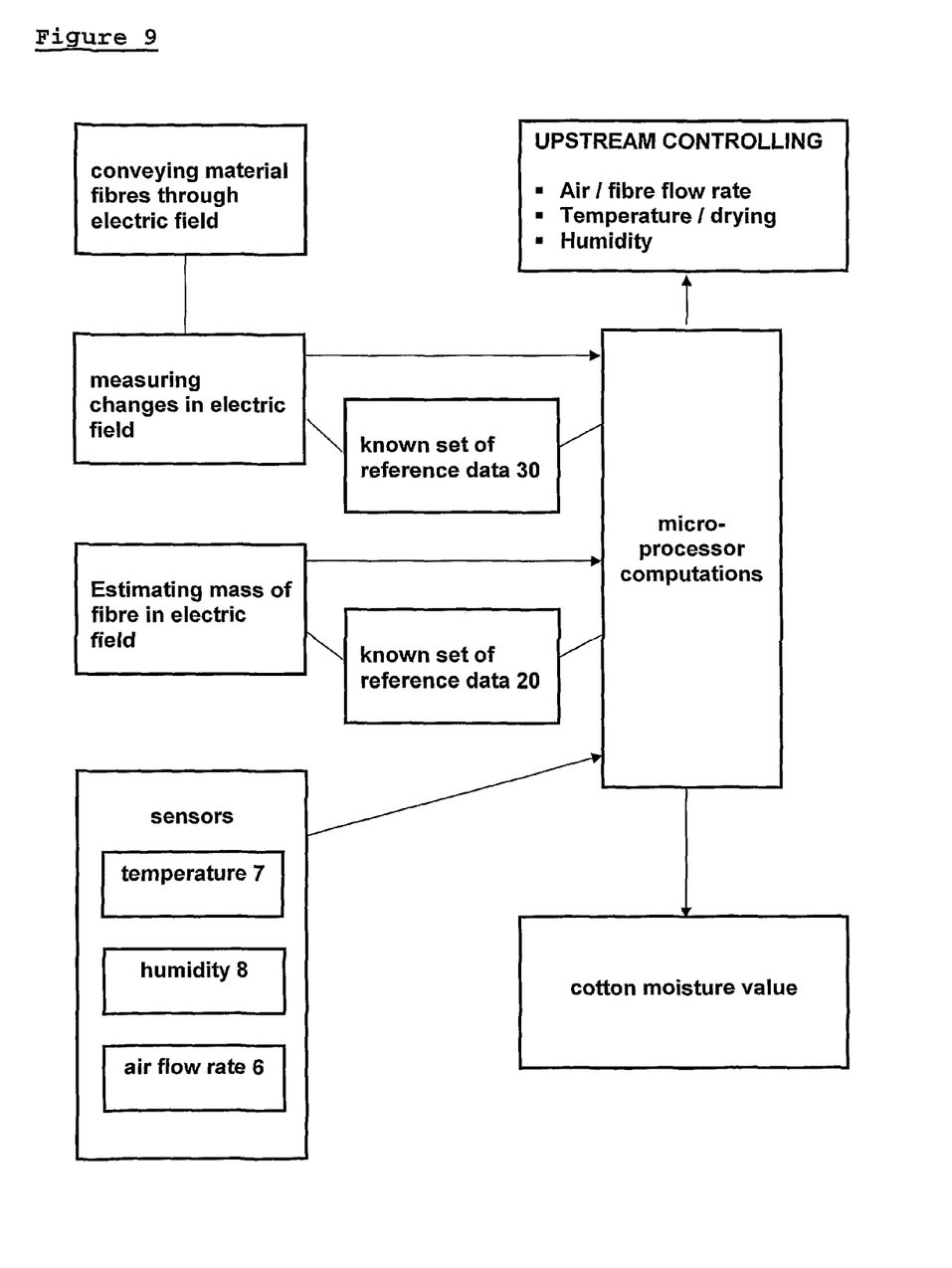
FIG. 9 is a block diagram showing the process steps according to an alternative embodiment.

The preferred embodiment described above involves calculating the moisture content of cotton fibre in absolute terms using two outputs. In an alternative embodiment, the desired property of the material may be determined with reference to sets of known data that may be either pre-existing and publicly available data or data sets established by earlier trials. With reference to FIG. 9, the alternative embodiment may involve conveying material, such as cotton fibre through the electric field and measuring changes in the electric field. In addition, the process may involve estimating the mass of fibre being conveyed and suitably the mass of fibre conveyed through the electric field. Although estimating the mass of the fibre in the electric field may involve measuring the dielectric properties including changes caused by the fibre in another electric field, suitably estimating the mass of the fibre is carried out using a detecting device in the form of an optical detector which optically measures changes in light received by a light receiver caused by the fibre being conveyed between the light source and the light receiver. Output from the light receiver is communicated to the processing unit which in turn estimates the mass of fibre in the electric field at any one moment by comparing the signal to a known set of reference data that is retrievable by the micro-processor.

Changes in the electric field caused by the fibre relates to the mass of the fibre in the electric field and other physical properties such as moisture content in the fibre. The output of the electric field is normalised to remove the influence of mass of fibre in the electric field using the mass detected by the optical measurement.

Finally, the moisture content of the fibre is determined with reference to the normalized output of the electric field which may also include a comparison to another known set of reference data. The output signals of the capacitor and optical device may be used by a micro-processor form manipulating the output signals as described to arrive at the moisture content.

Other sensors can also be used for controlling moisture and mass flow, by feeding back via a PC or microprocessor, to the process feed and/or humidifier or dryer apparatuses of a gin (not shown in the Figures).

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. An apparatus for measuring the moisture content of a material, the apparatus including:
i) an electric field generator and when in use, the material whose moisture content is to be measured is disposed in the electric field and changes in the electric field caused by the material provides a first output that is related to at least two properties of the material, at least one of which is the moisture content and a second property;
ii) a temperature sensor for sensing temperature in the electric field and providing a temperature output;
iii) a humidity sensor for sensing humidity of the air within the electric field and providing a humidity output;
iv) a device that provides a second output that is related to the second property of the material; and
v) a processing unit that determines the moisture content of the material with reference to the first output, the second output, and the temperature and humidity outputs.

2. The apparatus according to claim 1, wherein the second property is the mass of material in or passing through the electric field.

3. The apparatus according to claim 1, wherein the apparatus includes a passageway through which the material being measured is conveyed pneumatically or by gravity.

4. The apparatus according to claim 3, wherein the electric field extends across the passageway and the first output is based on the changes in the electric field as the material is conveyed through the electric field.

5. The apparatus according to claim 1, wherein the device that provides the second output is an optical device that estimates the mass of the material in the electric field.

6. The apparatus according to claim 5, wherein the optical device comprises a light source and a light receiver that are arranged such that the material at least in part, is located between the light source and the light receiver and the second output is an output of the light receiver.

7. The apparatus according to claim 1, wherein the electric field generator includes a capacitor.

8. The apparatus according to claim 7, wherein the capacitor includes at least one pair of capacitor plates arranged opposite and parallel to each other with a space there between, whereby air and the material between the plates provides a dielectric.

9. The apparatus according to claim 1, wherein the apparatus further includes a converter that converts either one or a combination of the first and second signals from an analogue signal to a digital signal.

10. The apparatus according to claim 1, wherein the apparatus includes output converters adapted to transform the first output and second output into first and second output signals of the same type so that they can be directly compared.

11. The apparatus according to claim 1, wherein when the electric field is generated by a capacitor and the first output is a difference in capacitance, the apparatus includes a first converter that converts the first output to a voltage difference signal.

12. The apparatus according to claim 1, wherein when the second output is an output of an optical device, the apparatus includes a second converter that converts the second output from the optical device to a voltage signal.

13. The apparatus according to claim 12, wherein when the electric field is generated by a capacitor and the first output is a difference in capacitance, the apparatus includes a first converter that converts the first output to a voltage difference signal, and wherein the processing unit calculates the moisture content of the material with reference to: i) the first output signal and the second output signal, or ii) the voltage difference signal of the first converter and voltage signal of the second converter.

14. The apparatus according to claim 1, wherein when the electric field is generated by a capacitor and the first output is a difference in capacitance, the apparatus includes a first converter that converts the first output to a voltage difference signal, and wherein when the second output is an output of an optical device, the apparatus includes a second converter that converts the second output from the optical device to a voltage signal, the apparatus including conditioners for adjusting the magnitude of the first and second outputs and/or the voltage difference signal and the voltage signal to enable direct signal comparison.

15. The apparatus according to claim 1, wherein the processing unit estimates the relative humidity in the electric field from outputs of the temperature and humidity sensors.

16. The apparatus according to claim 15, wherein when the electric field is generated by a capacitor and the first output is a difference in capacitance, the apparatus includes a first converter that converts the first output to a voltage difference signal and when the second output is an output of an optical device, the apparatus includes a second converter that converts the second output from the optical device to a voltage signal, and wherein the processing unit calculates the moisture content as a function that includes variables based on:
the voltage difference signal of the first converter;
the voltage signal of the second converter; and
an estimate of the relative humidity in the electric field.

17. The apparatus according to claim 1, wherein the apparatus includes a flow sensor for sensing the flow rate of air in the electric field.

18. The apparatus according to claim 1, wherein the apparatus includes a shield about the electric field to prevent interference from other electromagnetic fields from external sources.

19. A process for determining moisture content of material, the process including the steps of:
a) introducing material into an electric field;
b) measuring changes in the electric field caused by the material introduced into the electric field in step a), wherein the change in electric field relates to the moisture content of the material and another property of the material in the electric field;
c) estimating the other property of the material;
d) measuring the temperature in the electric field;
e) measuring the humidity of the air within the electric field; and
f) determining a value for the moisture content using the changes in electric field measured in step b), the other property of the material from step c), and the temperature and humidity measurement from steps d) and e).

20. The process according to claim 19, wherein the process includes an initial step of generating the electric field.

21. The process according to claim 19, wherein step a) involves conveying the material through the electric field pneumatically or by gravity.

22. The process according to claim 19, wherein the change in electric field according to step b) relates to at least two properties of the material in the electric field, of which one is the moisture content and another is the mass of the material in the electric field.

23. The process according to claim 19, wherein the changes in the electric field are sensed as an output of the electric field generator.

24. The process according to claim 19, wherein the electric field is capacitively generated by a capacitor, or inductively generated by an inductor.

25. The process according to claim 24, wherein when changes in the electric field are measured by changes in capacitance of a capacitor that generates the electric field, the output of the capacitor is transformed from a capacitance difference into a voltage difference signal.

26. The process according to claim 19, wherein estimating the other property of the material according to step c) is based on an output of a device in which the output is representative of mass of the material sensed by the device.

27. The process according to claim 26, wherein the device is an optical device that includes a light source and a light receiver, and the output of the optical device is based on amount of light received by the light receiver which is dependent on light transmitted or reflected by the material.

28. The process according to claim 27, wherein when the other property of the material is based on the output of the optical device that represents the mass of the material in the electric field, the output of the optical device is transformed into a voltage signal.

29. The process according to claim 28, wherein when changes in the electric field are measured by changes in capacitance of a capacitor that generates the electric field, the output of the capacitor is transformed from a capacitance difference into a voltage difference signal, and wherein the magnitude of either one or both of the voltage difference signal and the voltage signal is adjusted to enable direct signal comparison of the voltage difference signal and the voltage signal.

30. The process according to claim 28, wherein when changes in the electric field are measured by changes in capacitance of a capacitor that generates the electric field, the output of the capacitor is transformed from a capacitance difference into a voltage difference signal, and wherein step f) includes calculating the moisture content of the material as a function of the voltage difference signal of the capacitor and the voltage signal of the optical device.

31. The process according to claim 30, wherein the magnitude of either one or both of the voltage difference signal and the voltage signal is adjusted to enable direct signal comparison of the voltage difference signal and the voltage signal, and wherein step f) includes calculating the moisture content of the material using the formula:

$$\text{Moisture} = f(M_{cap}, M_{light}, H, T) + k$$

wherein
- $M_{cap}$ is the mass indicated by the output of the capacitor such that voltage difference output signal (mentioned above),
- $M_{light}$ is the mass indicated by the output of the light sensor such as the voltage signal (mentioned above),
- H is the humidity,
- T is the temperature, and
- k is a constant representative of a number of parameters that will depend on the specific apparatus geometry and sensors.

32. The process according to claim 28, wherein the process also includes estimating the relative humidity of the air in the electric field using a humidity sensor and the output of a temperature sensor.

33. The process according to claim 32, wherein when changes in the electric field are measured by changes in capacitance of a capacitor that generates the electric field, the output of the capacitor is transformed from a capacitance difference into a voltage difference signal, and wherein the magnitude of either one or both of the voltage difference signal and the voltage signal is adjusted to enable direct signal comparison, and wherein step f) includes calculating moisture content of the material in the electric field as function of:
  i) the voltage difference signal of the capacitor;
  ii) the voltage signal of the optical device;
  iii) and the relative humidity estimation.

34. The process according to claim 33, wherein the electric field is of a strength that is suitable for measuring a moisture content up to 16% weight of cotton fiber.

35. The process according to claim 34, wherein step f) involves determining the moisture content to an accuracy of ±0.5% weight of water on the weight of cotton fiber.

36. The process according to claim 26, wherein the changes in the electric field are sensed as an output of the electric field generator, and wherein the method includes transforming the output of the electric field generator and the output of the device into first and second output signals of the same type so that the output signals can be directly compared.

37. The process according to claim 19, wherein step f) is performed using a processing unit.

38. The process according to claim 19, wherein the process includes controlling the flow rate of material passing through the electric field.

39. The process according to claim 19, wherein the process includes controlling the humidity of the air passing through the electric field.

40. The process according to claim 19, wherein the process includes controlling the electric field.

41. An apparatus for measuring the moisture content of a material, the apparatus comprising:
  (i) a capacitor that generates an electric field and when in use, the material whose moisture content is to be measured is disposed in the electric field and changes in the capacitance caused by the material provides a first output that is related to at least two properties of the material, at least one of which is the moisture content and a second property, and a first converter converts the first output to a first voltage difference signal;
  (ii) a temperature sensor for sensing temperature in the electric field and providing a temperature output;
  (iii) a humidity sensor for sensing humidity of the air within the electric field and providing a humidity output;
  (iv) an optical device that provides a second output that is related to the second property of the material, and a second converter converts the second output from the optical device to a second voltage signal; and
  (v) a processing unit that determines the moisture content of the material with reference to the first voltage difference signal, the second voltage signal, and the temperature and humidity outputs.

* * * * *